US006468309B1

(12) United States Patent
Lieberman

(10) Patent No.: US 6,468,309 B1
(45) Date of Patent: Oct. 22, 2002

(54) METHOD AND APPARATUS FOR STABILIZING ADJACENT BONES

(75) Inventor: Isador H. Lieberman, Pepper Pike, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/708,292

(22) Filed: Nov. 8, 2000

Related U.S. Application Data
(60) Provisional application No. 60/238,265, filed on Oct. 5, 2000.

(51) Int. Cl.[7] .................................................. A61F 2/44
(52) U.S. Cl. ...................................... 623/17.11; 606/77
(58) Field of Search ........................... 623/16.11, 17.11, 623/17.16; 606/61, 65

(56) References Cited

U.S. PATENT DOCUMENTS

| 2,033,039 A | | 3/1936 | Limpert |
| 4,762,453 A | | 8/1988 | DeCaro |
| 4,854,311 A | | 8/1989 | Steffee |
| 4,961,740 A | | 10/1990 | Ray et al. |
| 5,055,104 A | | 10/1991 | Ray |
| 5,263,953 A | | 11/1993 | Bagby |
| 5,489,308 A | * | 2/1996 | Kuslich et al. ............... 623/17 |

(List continued on next page.)

FOREIGN PATENT DOCUMENTS

| EP | 0374088 A1 | 6/1990 |
| EP | 0663184 A1 | 7/1995 |
| FR | 2299548 | 8/1976 |
| SU | 1071297 A | 2/1984 |
| WO | WO0224087 A1 | 3/2002 |

OTHER PUBLICATIONS

An article entitled "Anterior Vertebral Body Screw Pullout Testing, A Comparison of Zielke, Kaneda, Universal Spine System, and Universal Spine System with Pullout–Resistant Nut", by Isador H. Lieberman et al., reprinted from SPINE, vol. 23, No. 8, Apr. 15, 1998.

Primary Examiner—David H. Willse
Assistant Examiner—Javier G. Blanco
(74) Attorney, Agent, or Firm—Tarolli, Sundheim, Covell, Tummino & Szabo L.L.P.

(57) ABSTRACT

An apparatus (10) is provided for implantation into an adjacent pair of vertebral bodies (12 and 14) having first and second surfaces (17 and 19) that oppose each other. The apparatus (10), when implanted, is attached to the adjacent pair of vertebral bodies and stabilizes the vertebral bodies (12 and 14) while the vertebral bodies fuse together. The apparatus (10) comprises a platform (24) having a third surface (38) extending transverse to the first and second surfaces (17 and 19). The apparatus (10) further comprises at least one helical spike (50, 52) for embedding into each of the adjacent pair of vertebral bodies (12 and 14) upon rotation of the platform (24) to attach the helical spike to each of the vertebral bodies and thus fasten the vertebral bodies together. The helical spike (50, 52) projects from the platform (24) and extends around a longitudinal axis (22). The helical spike (50, 52) has a tip portion (58) at a distal end (62) for penetrating the first and second surfaces (17 and 19) and for screwing into the adjacent pair of vertebral bodies (12 and 14) as the platform (24) is rotated. The helical spike (50, 52) at least partially defines an internal cavity (140) for receiving material (130) that promotes fusion of the vertebral bodies (12 and 14).

12 Claims, 5 Drawing Sheets

U.S. PATENT DOCUMENTS

| | | | |
|---|---|---|---|
| 5,534,031 A | * | 7/1996 | Matsuzaki et al. ....... 623/17.11 |
| 5,582,616 A | | 12/1996 | Bolduc et al. |
| 5,626,613 A | | 5/1997 | Schmieding |
| 5,662,683 A | | 9/1997 | Kay |
| 5,728,116 A | | 3/1998 | Rosenman |
| 5,800,550 A | | 9/1998 | Sertich |
| 5,810,851 A | | 9/1998 | Yoon |
| 5,824,008 A | | 10/1998 | Bolduc et al. |
| 5,888,223 A | | 3/1999 | Bray, Jr. |
| 5,904,696 A | | 5/1999 | Rosenman |
| 6,010,502 A | | 1/2000 | Bagby |
| 6,036,701 A | | 3/2000 | Rosenman |
| 6,071,310 A | | 6/2000 | Picha et al. |
| 6,080,155 A | | 6/2000 | Michelson |
| 6,102,950 A | | 8/2000 | Vaccaro |
| 6,106,557 A | | 8/2000 | Robioneck et al. |
| 6,113,638 A | | 9/2000 | Williams et al. |
| 6,120,502 A | | 9/2000 | Michelson |
| 6,120,503 A | | 9/2000 | Michelson |
| 6,123,505 A | | 9/2000 | Michelson |
| 6,126,688 A | | 10/2000 | McDonnell |
| 6,126,689 A | | 10/2000 | Brett |
| 6,296,656 B1 | | 10/2001 | Bolduc et al. |

* cited by examiner

METHOD AND APPARATUS FOR STABILIZING ADJACENT BONES

This application claims the benefit of provisional application No. 60/238,265, filed Oct. 5, 2000.

TECHNICAL FIELD

The present invention is directed to a method and apparatus for stabilizing adjacent bones, and is particularly directed to a method and apparatus for attaching and stabilizing adjacent vertebral bodies while the vertebral bodies fuse together.

BACKGROUND OF THE INVENTION

Each adjacent pair of vertebrae in the human spinal column are separated by an intervertebral disc that makes relative movement of the vertebrae possible. Problems, however, can develop with one or more of the discs, causing severe back pain. In some cases, it is necessary to remove a problematic disc and to fuse the adjacent vertebrae together in order to relieve pain.

One known method for fusing an adjacent pair of vertebrae following removal of a disc is to implant a device, commonly referred to as a fusion cage, into the interbody space where the disc was removed. The fusion cage facilitates fusion of the vertebrae. Typically, procedures such as reaming and/or tapping of adjacent vertebrae are required to prepare the adjacent vertebrae to receive the fusion cage. Such procedures normally involve substantial cutting of the hard cortical bone of the end plates of the adjacent vertebrae, which can weaken the end plates and lead to collapse of the vertebrae. The fusion cage is then positioned in the interbody space and into engagement with the adjacent vertebrae. At least one known fusion cage has relatively movable parts that enable the fusion cage to be expanded after the fusion cage is positioned in the interbody space between adjacent vertebrae. The design of this expandable fusion cage is, however, relatively complex.

Typically, a fusion cage includes an internal cavity that is filled with bone graft material. The fusion cage and the bone graft material promote bone growth that slowly unites the adjacent vertebrae. The typical fusion cage, while in engagement with the adjacent vertebrae, does not attach to the vertebrae and thus does not resist relative movement of the vertebrae, through bending or rotation, along any one of the three planes of motion (sagittal, coronal, or horizontal). Rather, the typical fusion page relies on the viscoelasticity of the surrounding ligaments to stabilize the adjacent vertebrae.

It is desirable to provide an apparatus for implantation into an adjacent pair of vertebral bodies that attaches to and thus fastens the vertebral bodies while they fuse together despite the forces on the apparatus from human body movement and muscle memory. It is further desirable to provide an apparatus which has a simple one-piece construction and which may be implanted into an adjacent pair of vertebrae without having to prepare the adjacent vertebrae to accept the apparatus by substantial cutting of the cortical bone.

SUMMARY OF THE INVENTION

The present invention is an apparatus for implantation into an adjacent pair of vertebral bodies having first and second surfaces that oppose each other. The apparatus, when implanted, is attached to the adjacent pair of vertebral bodies and stabilizes the vertebral bodies while the vertebral bodies fuse together. The apparatus comprises a platform having a third surface extending transverse to the first and second surfaces. The apparatus further comprises at least one helical spike for embedding into each of the adjacent pair of vertebral bodies upon rotation of the platform to attach the at least one helical spike to each of the vertebral bodies and thus fasten (pin) the vertebral bodies together. The at least one helical spike projects from the platform and extends around a longitudinal axis. The at least one helical spike has a tip portion at a distal end for penetrating the first and second surfaces and for screwing into the adjacent pair of vertebral bodies as the platform is rotated. The at least one helical spike at least partially defines an internal cavity for receiving material that promotes fusion of the vertebral bodies.

In accordance with one embodiment of the present invention, the apparatus comprises a pair of helical spikes. The proximal ends of the pair of helical spikes are spaced 180° apart.

In accordance with another embodiment of the present invention, the apparatus comprises three helical spikes extending around the longitudinal axis. The proximal ends of the three helical spikes are spaced 120° apart.

The present invention also provides a method for attaching and stabilizing an adjacent pair of vertebral bodies while the vertebral bodies fuse together, the vertebral bodies having first and second surfaces that oppose each other. The method comprises the step of removing disc material disposed between the vertebral bodies to create an interbody space and the step of providing an interbody stabilizer for insertion into the interbody space by implanting the interbody stabilizer into both of the adjacent pair of vertebral bodies. The interbody stabilizer comprises a platform and at least one helical spike. The platform has a third surface extending transverse to the first and second surfaces of the vertebral bodies. The at least one helical spike projects from the platform and extends around a longitudinal axis. The at least one helical spike at least partially defines an internal cavity for receiving material that promotes fusion of the vertebral bodies. The method further comprises the step of embedding the interbody stabilizer into each of the adjacent pair of vertebral bodies by rotating the platform of the interbody stabilizer. Rotation of the platform causes the at least one helical spike to penetrate into and subsequently out of each of the vertebral bodies in an alternating manner to attach the interbody stabilizer to each of the vertebral bodies and thus fasten (pin) the vertebral bodies together. Material that promotes fusion of the vertebral bodies is placed into the internal cavity in the interbody stabilizer.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF PREFERRED EMBODIMENTS

Figure 1:
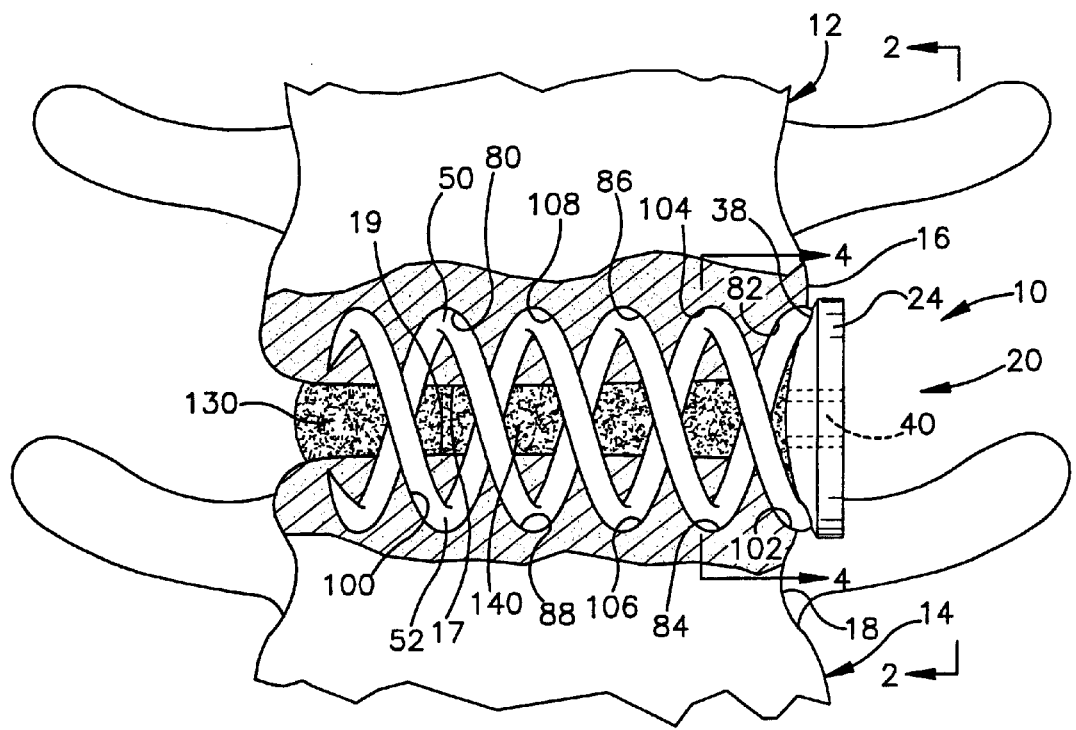
FIG. 1 is a schematic anterior view of an apparatus implanted in an adjacent pair of vertebral bodies in accordance with the present invention.
Figure 2:
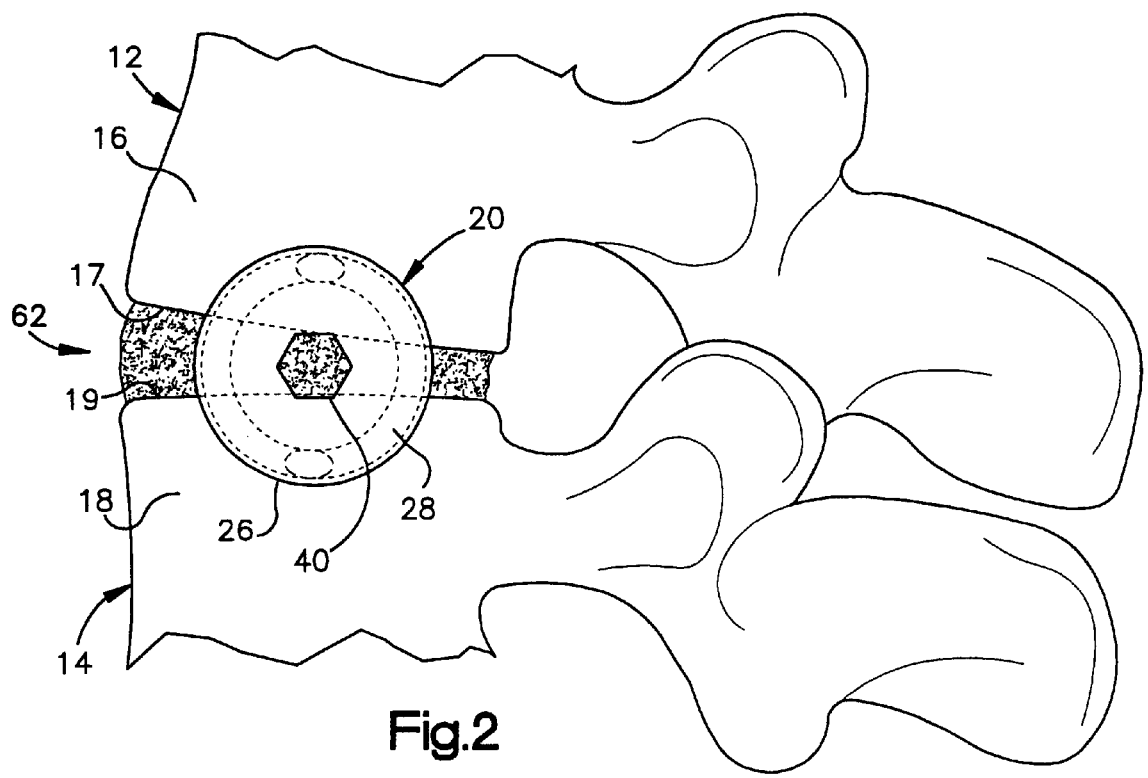
FIG. 2 is a side view taken along line 2—2 in FIG. 1.

The present invention is directed to a method and apparatus for stabilizing adjacent bones, and is particularly directed to a method and apparatus for attaching and stabilizing adjacent vertebral bodies while the vertebral bodies fuse together. As representative of the present invention, FIG. 1 illustrates an apparatus 10 implanted into an adjacent pair of lumbar vertebrae 12 and 14 in a vertebral column (not shown). It should be understood that the apparatus 10 could be implanted into any adjacent pair of vertebrae. The vertebrae 12 has a side surface 16 and a lower surface (or end plate) 17 (FIG. 2). The vertebrae 14 has a side surface 18 and an upper surface (or end plate) 19.

Figure 3:
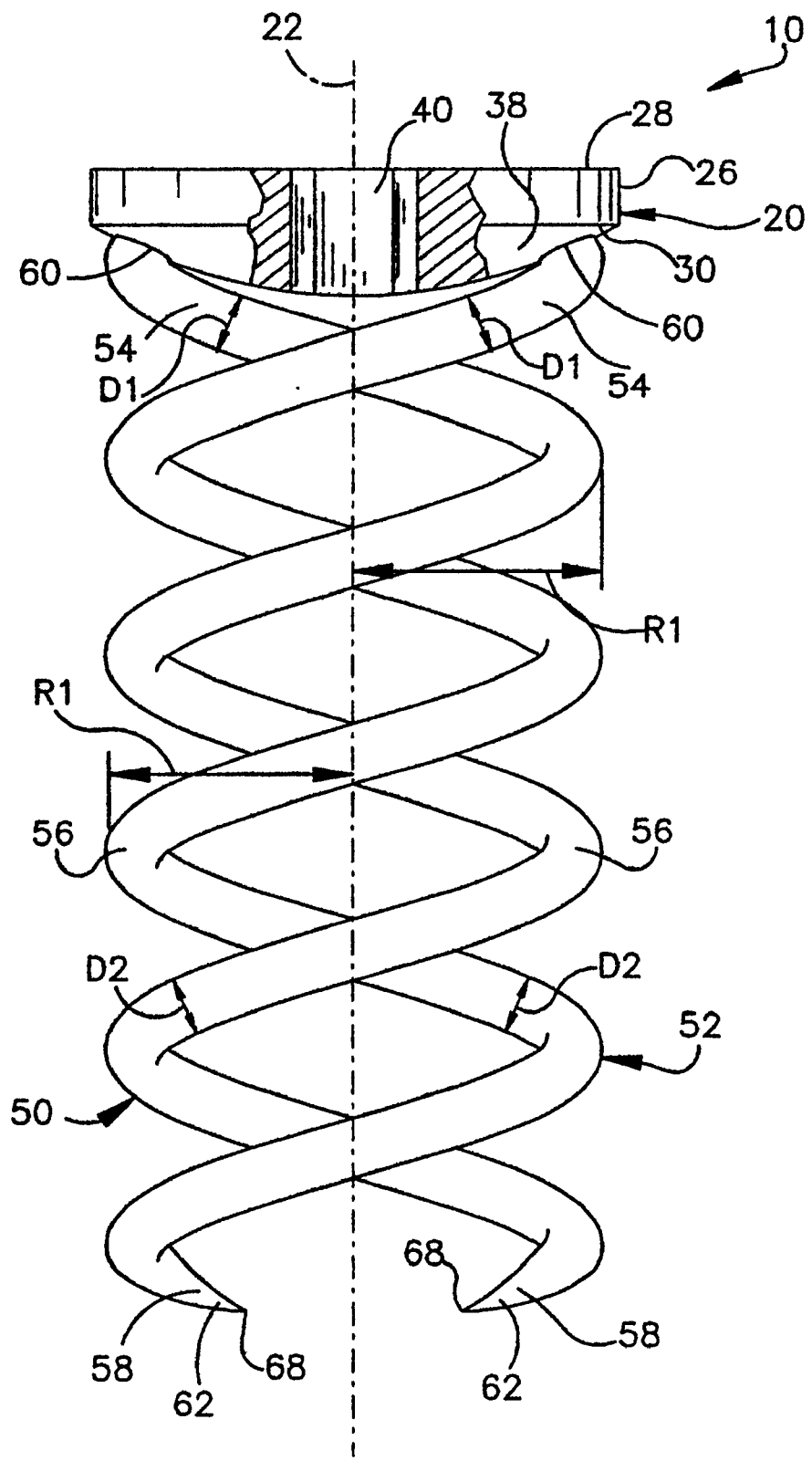
FIG. 3 is a perspective view of the apparatus of FIG. 1.

The apparatus 10 comprises an interbody stabilizer 20 made from a biocompatible material, such as titanium or stainless steel. It is contemplated that the biocompatible material used to make the interbody stabilizer 20 could also be biodegradable. The interbody stabilizer 20 is centered about a longitudinal axis 22 (FIG. 3). The interbody stabilizer 20 includes a platform 24 having a generally cylindrical outer surface 26 extending between oppositely disposed first and second ends 28 and 30. The second end 30 of the platform 24 includes an end surface 38 that extends transverse to the side surfaces 16 and 18 of the adjacent vertebrae 12 and 14, respectively. The end surface 38 of the platform 24 has a shape that is complimentary to the side surfaces 16 and 18 of the vertebrae 12 and 14, respectively.

The platform 24 of the interbody stabilizer 20 further includes an axial passage 40 that extends from the first end 28 to the end surface 38. The passage 40 has a hexagonal configuration for receiving a rotatable driver (not shown).

First and second helical spikes 50 and 52 project from the end surface 38 of the platform 24. The helical spikes 50 and 52 resemble a pair of intertwined corkscrews. According to the embodiment illustrated in FIGS. 1–4, the first and second helical spikes 50 and 52 extend around the axis 22. The spikes 50 and 52 extend in a helical pattern about the axis 22 at the same, constant radius R1. It is contemplated, however, that the first and second helical spikes 50 and 52 could extend about the axis 22 at different radiuses. Further, it is contemplated that the radius of one or both of the first and second helical spikes 50 and 52 could increase or decrease as the helical spikes extend away from the platform 24. In order for the interbody stabilizer 20 to be implanted endoscopically through a typical cannula (not shown), it is preferred that the platform 24 and the helical spikes 50 and 52 are less than 20 mm in overall diameter. It should be understood that the interbody stabilizer 20 could have an overall diameter that is greater than 20 mm for certain applications, and that the interbody stabilizer could also be implanted in an open surgical procedure. However, for structural stability reasons, the overall diameter of the helical spikes 50 and 52 should remain less than or equal to the diameter of the platform 24.

In the illustrated embodiment of FIGS. 1–4, the first and second helical spikes 50 and 52 have the same axial length, and also have the same circular cross-sectional shape. It is contemplated, however, that the first and second helical spikes 50 and 52 could have different axial lengths. Further, it is contemplated that the helical spikes 50 and 52 could have a different cross-sectional shape, such as an oval shape. It also contemplated that the first and second helical spikes 50 and 52 could have different cross-sectional shapes and/or areas (i.e., one spike being thicker than the other spike). Finally, it is contemplated that the helical spikes 50 and 52 should have the same pitch, and that the pitch of the helical spikes would be selected based on the specific surgical application and quality of the bone in which the interbody stabilizer 20 is to be implanted.

Each of the first and second helical spikes 50 and 52 can be divided into three portions: a connecting portion 54, an intermediate portion 56, and a tip portion 58. The connecting portion 54 of each of the helical spikes 50 and 52 is located at a proximal end 60 that adjoins the end surface 38 of the platform 24. The connecting portion 54 may include barbs (not shown) for resisting pull-out of the helical spikes 50 and 52 from the vertebrae 12 and 14. According to one method for manufacturing the interbody stabilizer 20, the connecting portion 54 of each of the helical spikes 50 and 52 is fixedly attached to the platform 24 by inserting, in a tangential direction, the proximal ends 60 of the helical spikes into openings (not shown) in the end surface 38 and welding the connecting portions 54 to the platform. The inserted proximal ends 60 of the helical spikes 50 and 52 help to reduce tensile bending stresses on the helical spikes under a tensile load.

Alternatively, the helical spikes 50 and 52 may be formed integrally with the platform 24, such as by casting the interbody stabilizer 20. If the interbody stabilizer 20 is cast, it is contemplated that a fillet (not shown) may be added at the junction of the helical spikes 50 and 52 and the platform 24 to strengthen the junction and minimize stress concentrations at the connecting portions 54. The fillet at the junction of the helical spikes 50 and 52 and the platform 24 also helps to reduce bending stresses in the connecting portions 54 of the helical spikes under a tensile load.

Figure 4:
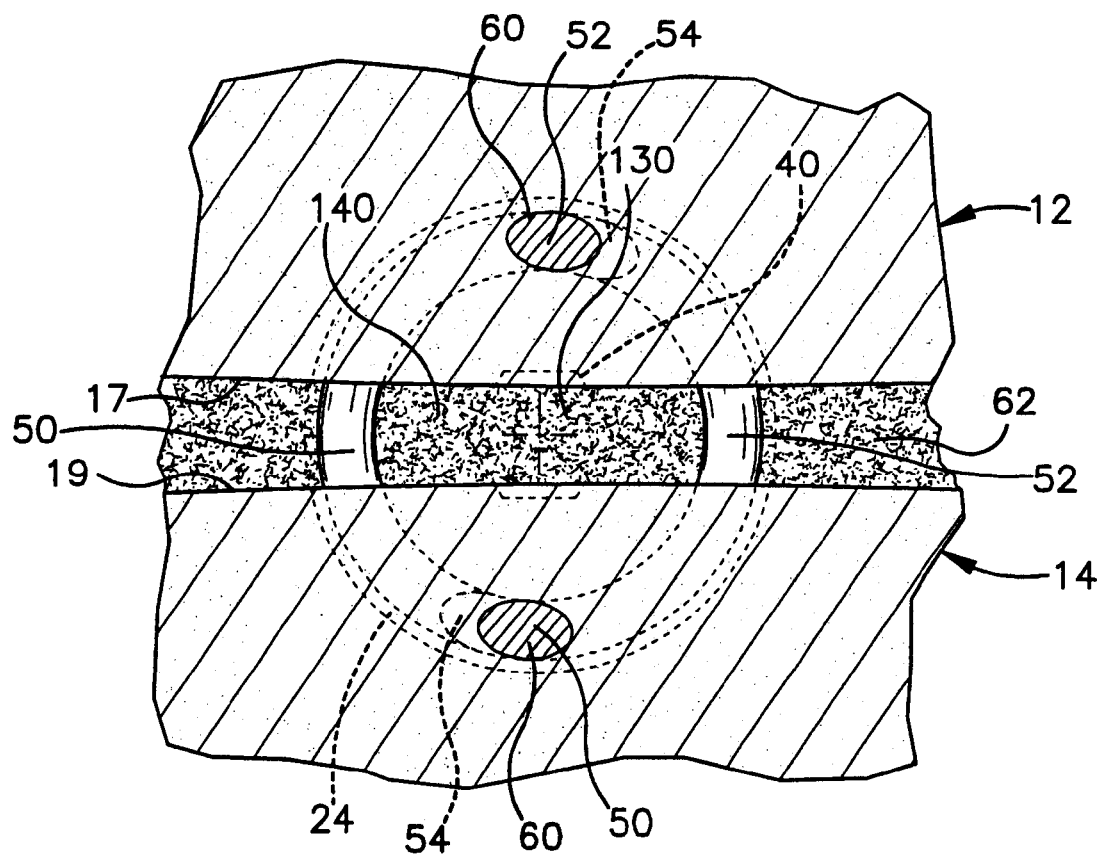
FIG. 4 is a sectional view taken along 4—4 in FIG. 1.

As best seen in FIG. 4, the connecting portions 54 at the proximal ends 60 of the first and second helical spikes 50 and 52 are spaced 180° apart about the axis 22 to balance the interbody stabilizer 20 and evenly distribute loads on the helical spikes. The connecting portion 54 of each of the helical spikes 50 and 52 has a first cross-sectional diameter D1 (FIG. 3).

The tip portion 58 of each of the helical spikes 50 and 52 is located at a distal end 62 of the helical spikes. The intermediate portion 56 of each of the helical spikes 50 and 52 extends between the tip portion 58 and the connecting portion 54. The intermediate portion 56 and the tip portion 58 of each of the helical spikes 50 and 52 has a second cross-sectional diameter D2 that is less than or equal to the first cross-sectional diameter D1 of the connecting portions 54. If the second cross-sectional diameter D2 is less than the first cross-section diameter D1, the increased thickness of the connecting portions 54 of the helical spikes 50 and 52 will help to provide the interbody stabilizer 20 with increased tensile strength at the junction of the helical spikes and the platform 24.

Figure 5:
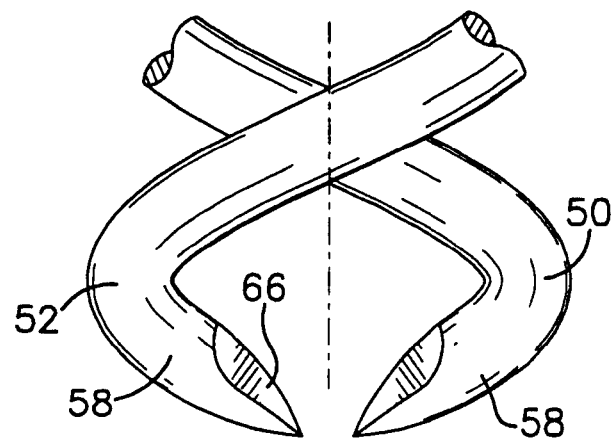
FIG. 5 illustrates an alternate configuration for an end portion of the apparatus of FIG. 1.

The tip portion 58 of each of the helical spikes 50 and 52 is self-penetrating and provides the helical spikes with the ability to penetrate into a respective one of the vertebrae 12 and 14 as the platform 24 of the interbody stabilizer 20 is rotated in a clockwise direction. The tip portions 58 illustrated in FIGS. 1–4 have an elongated conical shape with a sharp pointed tip 68. FIG. 5 illustrates an alternative, self-tapping configuration for the tip portions 58 which includes a planar surface 66 for driving into the vertebrae 12 and 14, in the same manner that a wood chisel turned upside-down drives into wood, as the platform 24 is rotated. It is contemplated that the tip portions 58 could also have a pyramid shape, similar to the tip of a nail.

FIGS. 1 and 2 illustrate the interbody stabilizer 20 implanted in the adjacent lumbar vertebrae 12 and 14 to stabilize the vertebrae. First, disk material that normally separates the vertebrae 12 and 14 is removed by the surgeon. Removal of the disk material leaves an interbody space 62 (FIG. 2) between the vertebrae 12 and 14. A tool (not shown) is then used to punch a hole (not shown) in the cortical bone (not shown) of each of the vertebrae 12 and 14. The hole in the vertebrae 12 may be punched in either the side surface 16 or the lower surface 17. The hole in the vertebrae 14 may be punched in either the side surface 18 or the upper surface 19. The holes in the vertebrae 12 and 14 are punched in locations that correspond to the spacing of the tip portions 58 of the helical spikes 50 and 52 of the interbody stabilizer 20. The holes in the vertebrae 12 and 14 are intended to make the initial rotation of the stabilizer 20 easier. It should be noted that one or both of the configurations of the tip portions 58 illustrated in FIGS. 1–5 may be able to punch through the cortical bone upon rotation of the interbody stabilizer 20, thus eliminating the need for the aforementioned tool to punch holes in the cortical bone.

The tip portions 58 of the interbody stabilizer 20 are placed in the holes in the vertebrae 12 and 14 and a rotatable driver (not shown) is inserted into the passage 40 in the platform 24. The driver is then rotated, causing the interbody stabilizer 20 to rotate as well. It is contemplated that a cylindrical sleeve (not shown) may be placed around the intermediate portions 56 and the connecting portions 54 of the helical spikes 50 and 52 to prevent the helical spikes from deforming radially outward during the initial rotation of the interbody stabilizer 20.

Rotation of the interbody stabilizer 20 screws the helical spikes 50 and 52 into the vertebrae 12 and 14, respectively. The tangentially-oriented connection between the connection portions 54 of the helical spikes 50 and 52 and the platform 24 minimizes bending loads on the connecting portions during rotation of the interbody stabilizer 20. Further, the tangentially-oriented connection ensures that the force vector resulting from axial force torque and applied by the driver to the platform 24 is transmitted along the helical centerline (not shown) of each of the helical spikes 50 and 52.

As the interbody stabilizer 20 is rotated, the tip portion 58 of the first helical spike 50 penetrates the cancellous bone in the vertebrae 12 and cuts a first helical segment 82 of a first tunnel 80 (FIG. 1) in the vertebrae 12. Simultaneously, the tip portion 58 of the second helical spike 52 penetrates the cancellous bone of the vertebrae 14 and cuts a first helical segment 102 of a second tunnel 100 in the vertebrae 14.

At some point between 90° and 180° of rotation of the interbody stabilizer 20, the tip portions 58 of the helical spikes 50 and 52 penetrate back out of the vertebrae 12 and 14, respectively and into the interbody space 62. More specifically, the tip portion 58 of the first helical spike 50 projects through the lower surface 17 of the vertebrae 12 and into the interbody space 62. Simultaneously, the tip portion 58 of the second helical spike 52 projects through the upper surface 19 of the vertebrae 14 and into the interbody space 62.

As the interbody stabilizer 20 is rotated beyond 180°, the tip portions 58 of the helical spikes 50 and 52 move through the interbody space 62 and engage the vertebrae 14 and 12, respectively. The tip portion 58 of the first helical spike 50 penetrates into the upper surface 19 of the vertebrae 14, while the tip portion 58 of the second helical spike 52 projects through the lower surface 17 of the vertebrae 12. Continued rotation of the interbody stabilizer 20 causes the tip portion 58 of the first helical spike 50 to cut a second helical segment 84 of the first tunnel 80 in the vertebrae 14. Similarly, the continued rotation causes the tip portion 58 of the second helical spike 52 to cut a second helical segment 104 of the second tunnel 100 in the vertebrae 12.

After another 90° to 180° of rotation of the interbody stabilizer 20, the tip portions 58 of the helical spikes 50 and 52 penetrate back out of the vertebrae 14 and 12, respectively, and into the interbody space 62. More specifically, the tip portion 58 of the first helical spike 50 projects through the upper surface 19 of the vertebrae 14 and the tip portion 58 of the second helical spike 52 projects through the lower surface 17 of the vertebrae 12.

As the interbody stabilizer 20 is rotated further, t he tip portions 58 of the helical spikes 50 and 52 move through the interbody space 62 and re-engage the vertebrae 12 and 14, respectively. The tip portion 58 of the firs t helical spike 50 penetrates the lower surface 17 of the vertebrae 12 and cuts a third helical segment 86 of the first tunnel 80 in the vertebrae 12. Simultaneously, the tip portion 58 of the second helical spike 52 penetrates the upper surface 19 of the vertebrae 14 and cuts a third helical segment 106 of the second tunnel 100 in the vertebrae 14.

After further rotation of the interbody stabilizer 20, the tip portions 58 of the helical spikes 50 and 52 a gain penetrate back out of the vertebrae 12 and 14, respectively and into the interbody space 62. The tip portion 58 of the first helical spike 50 projects through the lower surface 17 of the vertebrae 12, while the tip portion 58 of the second helical spike 52 projects through the upper surface 19 of the vertebrae 14. The interbody stabilizer 20 is then rotated so that the tip portions 58 of the helical spikes 50 and 52 move through the interbody space 62 and re-engage the vertebrae 14 and 12, respectively. The tip portion 58 of the first helical spike 50 again penetrates into the upper surface 19 of the vertebrae 14, causing the tip portion 58 of the first helical spike 50 to cut a fourth helical segment 88 of the first tunnel 80 in the vertebrae 14. Similarly, the tip portion 58 of the second helical spike 52 again penetrates through the lower surface 17 of the vertebrae 12, causing the tip portion 58 of the second helical spike 52 to cut a fourth helical segment 108 of the second tunnel 100 in the vertebrae 12.

This pattern of screwing the helical spikes 50 and 52 of the interbody stabilizer 20 into and out of each of the vertebrae 12 and 14 in an alternating manner continues with each revolution of the platform 24 by the driver. The continued rotation of the platform 24 embeds the helical spikes 50 and 52 of the interbody stabilizer 20 into the vertebrae 12 and 14 and attaches the interbody stabilizer to each of the vertebrae. With each rotation of the interbody stabilizer 20, the connection between the interbody stabilizer and each of the vertebrae 12 and 14 gets stronger. The attachment of the interbody stabilizer 20 to each of the vertebrae 12 and 14 thus fastens, or pins, the vertebrae together, yet spaced apart. Rotation of the platform 24 is terminated when the end surface 38 of the platform seats against one or both of the side surfaces 16 and 18 of the vertebrae 12 and 14, respectively.

Once the interbody stabilizer 20 is implanted, bone graft material 130 (shown schematically in FIGS. 1 and 2) for permanently fusing the vertebrae 12 and 14 is placed into the interbody space 62. More specifically, the bone graft material 130 is placed into a cavity 140 defined by the helical spikes 50 and 52, the lower surface 17 of the vertebrae 12, and the upper surface 19 of the vertebrae 14. The bone graft material 130, which may comprise bone chips and/or synthetic bone material, is placed into the cavity 140 through the axial passage 40 in the platform 24 of the interbody stabilizer 20. A sufficient amount of the bone graft material 130 is placed into the cavity 140 to fill not only the cavity, but also the entire interbody space 62.

When implanted, the interbody stabilizer 20 is attached to both of the vertebrae 12 and 14 and securely fastens the vertebrae together. Because each of the helical spikes 50 and 52 penetrates into and subsequently out of each of the vertebrae 12 and 14, the helical spikes provide multiple fixation locations between the interbody stabilizer 20 and the vertebrae that pin the vertebrae together. The interbody stabilizer 20 is therefore able to resist relative movement of the vertebrae 12 and 14 toward or away from each other, and does not rely on surrounding ligaments to stabilize the vertebrae. More specifically, the interbody stabilizer 20 resists relative movement of the vertebrae 12 and 14, through bending or rotation, along any one of the three planes of motion (sagittal, coronal, or horizontal). Thus, the interbody stabilizer 20 is able to maintain proper intervertebral spacing and provide effective temporary stabilization of the adjacent vertebrae 12 and 14, despite substantial forces on the interbody stabilizer caused by human body movement and muscle memory, while the bone graft material 130 fuses the vertebrae together. Advantageously, the interbody stabilizer 20 has a simple one-piece construct and does not require substantial cutting of cortical bone (i.e., a reaming or tapping procedure) to prepare the vertebrae 12 and 14 to accept the interbody stabilizer. Thus, the interbody stabilizer 20 is not only a simplified construct, but also simplifies the steps required for implantation into adjacent vertebrae.

Figure 6:
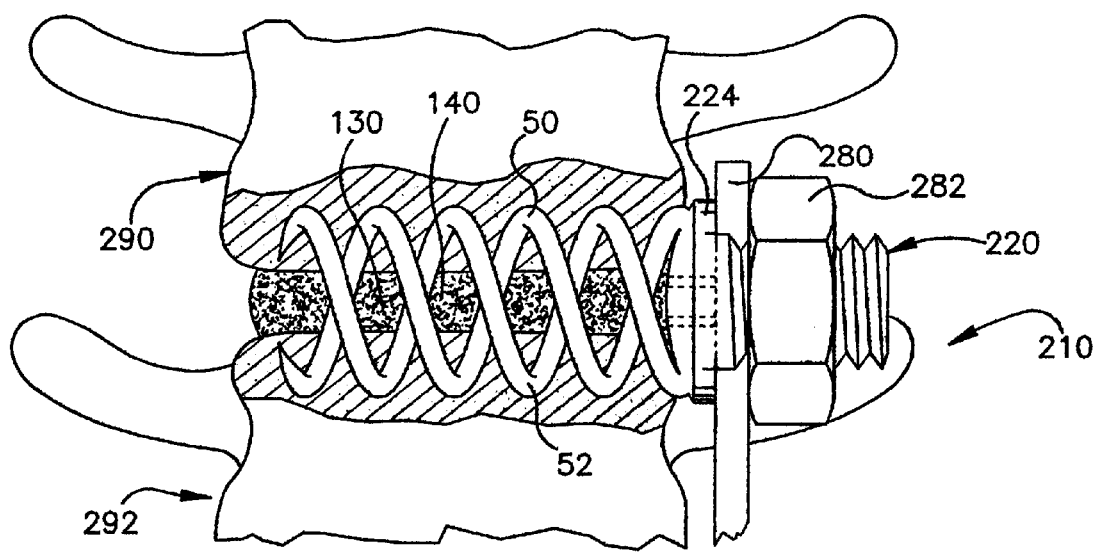
FIG. 6 is a schematic anterior view illustrating a second embodiment of the present invention.
Figure 7:
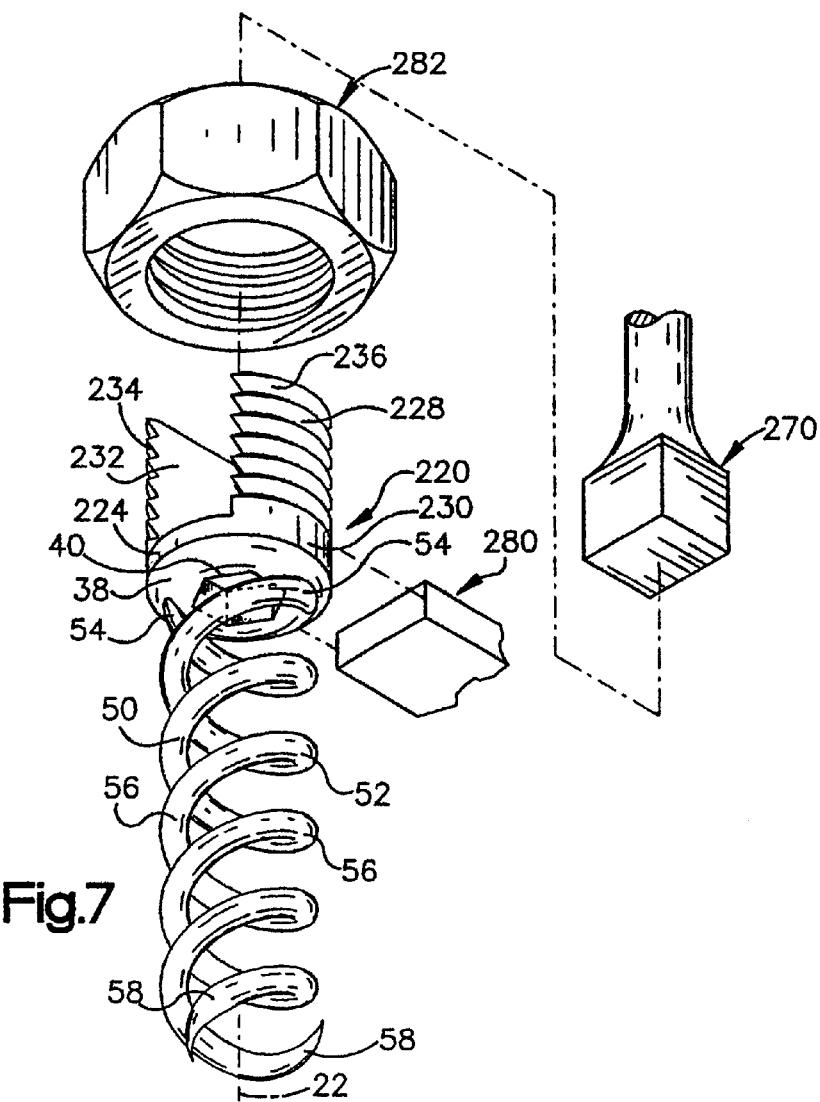
FIG. 7 is an exploded perspective view of the apparatus of FIG. 6, and includes a driver for rotating the apparatus.

FIGS. 6 and 7 illustrate an apparatus 210 constructed in accordance with a second embodiment of the present invention. In the second embodiment of FIGS. 6 and 7, reference numbers that are the same as those used in the first embodiment of FIGS. 1–4 designate parts that are the same as parts in the first embodiment.

According to the second embodiment, the apparatus 210 comprises an interbody stabilizer 220 having a platform 224. The platform 224 includes a generally rectangular slot 232 that extends axially from a first end 228 toward a second end 230 of the platform. Adjacent the first end 228, the platform 224 includes first and second segments of external threads 234 and 236 that are separated by the slot 232. The slot 232 and the threads 234 and 236 provide structure for connecting spinal fixation instrumentation to the platform 224. The first and second helical spikes 50 and 52 project from the end surface 38 at the second end 230 of the platform 224.

FIG. 6 illustrates how the interbody stabilizer 220 may be used for segmental spinal fixation. Lumbar vertebrae L3 and L4, indicated by reference numbers 290 and 292, respectively, are shown in FIG. 6. The interbody stabilizer 220 according to the second embodiment of the present invention is implanted in the interbody space between the vertebrae 290 and 292. The interbody stabilizer 220 is implanted into the vertebrae 290 and 2 92 in much the same manner a s described above regarding the first embodiment. A rotatable driver 270 (FIG. 7) fits into the slot 232 in the interbody stabilizer 220 and is used to rotate the interbody stabilizer.

Once the interbody stabilizer 220 is implanted, spinal fixation instrumentation such as a beam 280 which has been bent into a desired shape by the surgeon, is placed into the slot 232 in the interbody stabilizer. A nut 282 is then screwed onto the threads 234 and 236 on the platform 224 and tightened to secure the beam 280 to the interbody stabilizer 220. As in the first embodiment, the interbody stabilizer 220 fastens the vertebrae 290 and 292 together and stabilizes the vertebrae until the bone graft material 130 placed in the cavity 140 defined inside each of the interbody stabilizers fuses the vertebrae. The beam 280 helps to further support the vertebrae 290 and 292 until the vertebrae fuse together.

Figure 8:
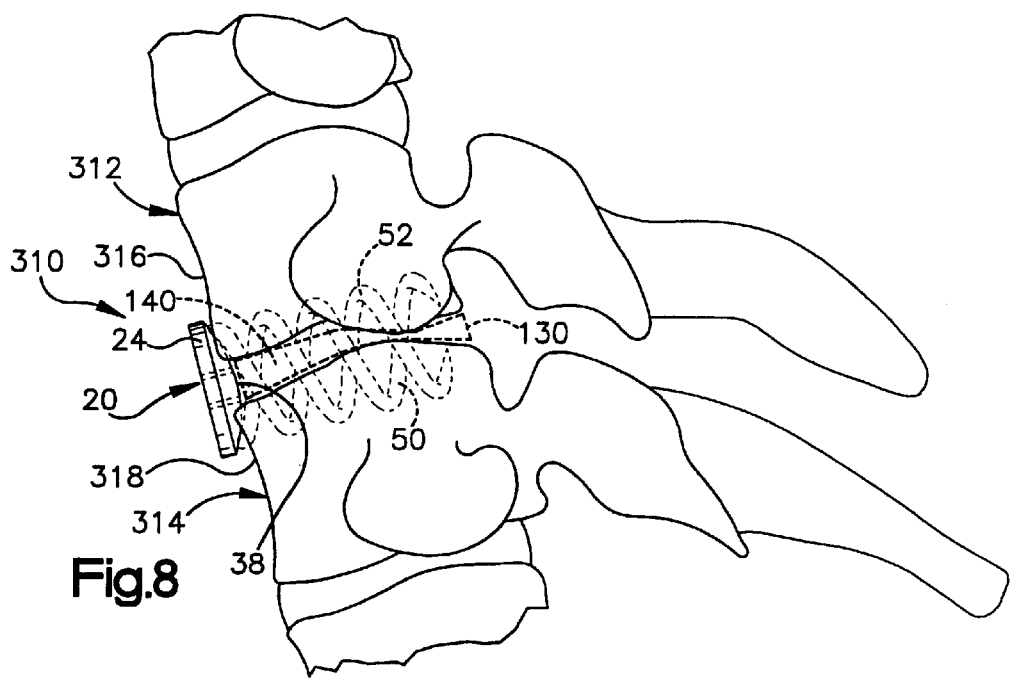
FIG. 8 is a side view illustrating a third embodiment of the present invention.

FIG. 8 illustrates an apparatus 310 constructed in accordance with a third embodiment of the present invention. In the third embodiment of FIG. 8, reference numbers that are the same as those used in the first embodiment of FIGS. 1–4 designate parts that are the same as parts in the first embodiment.

According to the third embodiment, the interbody stabilizer 20 is implanted into two cervical vertebrae 312 and 314 in the same manner as described above regarding the first embodiment. The end surface 38 of the interbody stabilizer 20 seats against anterior surfaces 316 and 318 of the vertebrae 312 and 314, respectively. As in the first embodiment, the interbody stabilizer 20 fastens the vertebrae 312 and 314 and stabilizes the vertebrae until the bone graft material 130 placed in the cavity 140 in the interbody stabilizer fuses the vertebrae.

Figure 9:
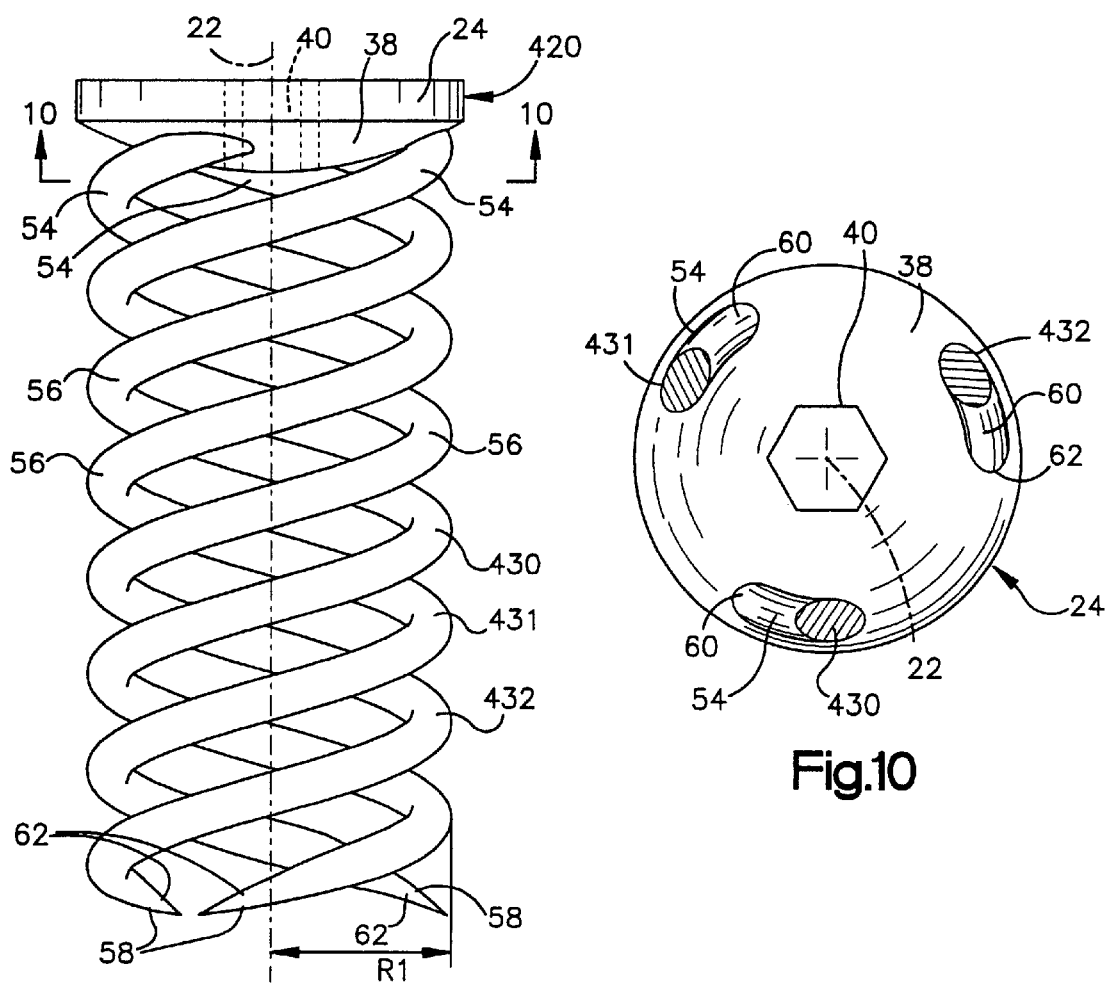
FIG. 9 is a side view illustrating a fourth embodiment of the present invention.
Figure 10:
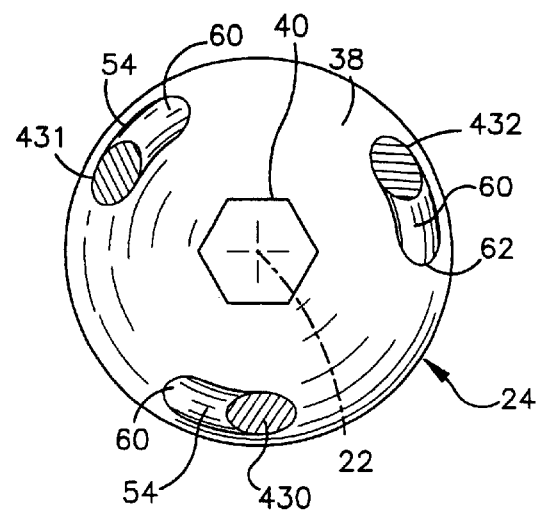
FIG. 10 is a sectional view taken along line 10—10 in FIG. 9.

FIGS. 9 and 10 illustrate an apparatus 410 constructed in accordance with a fourth embodiment of the present invention. In the fourth embodiment of FIGS. 9 and 10, reference numbers that are the same as those used in the first embodiment of FIGS. 1–4 designate parts that are the same as parts in the first embodiment.

According to the fourth embodiment, the apparatus 410 comprises an interbody stabilizer 420 having three helical spikes 430, 431, and 432 projecting tangentially from the end surface 38 of the platform 24. The spikes 430–432 are centered about the axis 22. As shown in FIG. 10, the connecting portions 54 at the proximal ends 60 of the helical spikes 430–432 are spaced 120° apart about the axis 22, which balances the interbody stabilizer 420 and evenly distributes loads on the helical spikes. As in the first embodiment of FIGS. 1–4, in the fourth embodiment of FIGS. 9 and 10, the cross-sectional diameter of the connection portions 54 of the helical spikes 430–432 is greater than or equal to the cross-sectional diameter of the intermediate portions 56 and the tip portions 58 of the helical spikes.

Each of the three helical spikes 430–432 extend in a helical pattern about the axis 22 at the same, constant radius R1. It is contemplated, however, that one or more of the helical spikes 430–432 could extend about the axis 22 at different radiuses. Further, it is contemplated that the radius of one or more helical spikes 430–432 could increase or decrease as the helical spikes extend away from the platform 24.

As shown in FIG. 9, the three helical spikes 430–432 have the same axial length and also have the same circular cross-sectional shape. It is contemplated, however, that one or more of the helical spikes 430–432 could have different axial lengths. Further, it is contemplated that one or more of the helical spikes 430–432 could have a different cross-sectional shape, such as an oval shape. It also contemplated that the one or more of the helical spikes 430–432 could have different cross-sectional shapes and/or areas (i.e., one spike being thicker or thinner than the other two spikes) .

Finally, it is contemplated that the helical spikes 430–432 should have the same pitch, and that the pitch of the helical spikes would be selected based on the specific surgical application and quality of the bone in which the interbody stabilizer 20 is to be implanted.

The tip portion 58 of each of the helical spikes 430–432 illustrated in FIG. 9 has an elongated conical shape for penetrating into a vertebrae as the platform 24 of the interbody stabilizer 420 is rotated in the clockwise direction. It should be understood that the tip portions 58 of the helical spikes 430–432 of the interbody stabilizer 420 could alternatively be configured like the tip portions illustrated in FIG. 5.

The interbody stabilizer 420 according to the fourth embodiment of FIGS. 9 and 10 is implanted into an adjacent pair of vertebrae in the same manner as the interbody stabilizer 20 according to the first embodiment. Further, the interbody stabilizer 420 according to the fourth embodiment may also be used to mount spinal fixation instrumentation as shown in the second embodiment of FIGS. 6 and 7. When implanted, the interbody stabilizer 420 is attached to both of the adjacent vertebrae and fastens the vertebrae together. Further, the interbody stabilizer 420 maintains proper intervertebral spacing and provides effective temporary stabilization of the adjacent vertebrae while the bone graft material placed in the cavity in the interbody stabilizer fuses the vertebrae together. Advantageously, the interbody stabilizer 420 is a simple one-piece construct does not require substantial cutting of cortical bone (i.e., a reaming or tapping procedure) to prepare the adjacent vertebrae to accept the interbody stabilizer.

It should be noted that the interbody stabilizers according to the present invention can be used not only to stabilize a degenerative disc, but can also be used to correct spinal deformity such as scoliosis, kyphosis, lordosis, and spondylosisthesis.

From the above description of the invention, those skilled in the art will perceive improvements, changes and modifications. It should be understood that the method and apparatus according to the present invention could be used to attach and stabilize other adjacent bones, not just bones in the spine or pelvis. Further, it is contemplated that the present invention could comprise a single helical spike, or more than three spikes. Such improvements, changes and modifications within the skill of the art are intended to be covered by the appended claims.

Having described the invention, I claim:

1. An apparatus for implantation into an adjacent pair of vertebral bodies having first and second surfaces, respectively, that oppose each other, said apparatus, when implanted, being attached to each of the vertebral bodies and stabilizing the vertebral bodies while the vertebral bodies fuse together, said apparatus comprising:

a platform having a third surface extending transverse to the first and second surfaces and transverse to a longitudinal axis of said apparatus; and at least two helical spikes shaped like intertwined corkscrews for embedding into each of the adjacent pair of vertebral bodies upon rotation of said platform to attach said at least two helical spikes to each of the vertebral bodies and thus fasten the vertebral bodies together, said at least two helical spikes projecting from said third surface of said platform and extending around said longitudinal axis, each of said at least two helical spikes having a connecting portion at a proximal end connected to said platform, said at least two helical spikes further having a tip portion at a distal end for penetrating the first and second surfaces and for screwing into the adjacent pair of vertebral bodies as said platform is rotated;

said at least two helical spikes at least partially defining an internal cavity for receiving material that promotes fusion of the vertebral bodies.

2. The apparatus of claim 1 wherein said platform includes an axially extending passage through which the material is placed into said internal cavity following implantation of said apparatus in the vertebral bodies.

3. The apparatus of claim 1 wherein said at least two helical spikes comprises a pair of helical spikes, said proximal ends of said pair of helical spikes being spaced 180° apart.

4. The apparatus of claim 1 wherein said at least two helical spikes comprises three helical spikes, said proximal ends of said three helical spikes being spaced 120° apart.

5. The apparatus of claim 1 wherein said platform includes structure for connecting spinal fixation instrumentation.

6. The apparatus of claim 1 wherein each of said at least two helical spikes has an intermediate portion extending between said connecting portion and said tip portion.

7. The apparatus of claim 6 wherein said intermediate portion of each of said at least two helical spikes has a first cross-sectional diameter and said connecting portion of each of said at least two helical spikes has a second cross-sectional diameter that is greater than said first cross-sectional diameter.

8. The apparatus of claim 6 wherein said intermediate portion of each of said at least two helical spikes has a first cross-sectional diameter and said connecting portion of each of said at least two helical spikes has a second cross-sectional diameter that is equal to said first cross-sectional diameter.

9. The apparatus of claim 1 wherein said platform and said at least two helical spikes are made of a biocompatible material.

10. The apparatus of claim 1 wherein said tip portion of each of said at least two helical spikes has a self-penetrating terminal end for penetrating into the bone as said platform is rotated.

11. A method for attaching and stabilizing an adjacent pair of vertebral bodies while the vertebral bodies fuse together, the pair of vertebral bodies having first and second surfaces, respectively, that oppose each other, said method comprising the steps of:

removing disc material disposed between the vertebral bodies to create an interbody space;

providing an interbody stabilizer for insertion into the interbody space by implanting the interbody stabilizer into both of the adjacent pair of vertebral bodies, the interbody stabilizer comprising a platform and at least two helical spikes that are shaped like intertwined corkscrews, the platform having a third surface extending transverse to the first and second surfaces of the vertebral bodies, the at least two helical spikes projecting from the third surface of the platform and extending around a common longitudinal axis, the at least two helical spikes at least partially defining an internal cavity for receiving material that promotes fusion of the vertebral bodies;

embedding each of the at least two helical spikes of the interbody stabilizer into the adjacent pair of vertebral bodies by rotating the platform of the interbody stabilizer which causes each of the at least two helical spikes to penetrate into and subsequently out of each of the vertebral bodies in an alternating manner to attach the interbody stabilizer to each of the vertebral bodies and thus fasten the vertebral bodies together; and placing material that promotes fusion of the vertebral bodies into the internal cavity in the interbody stabilizer.

12. The method of claim 11 further comprising the step of attaching spinal fixation instrumentation to the platform of the interbody stabilizer.

* * * * *